United States Patent [19]

Kiikka

[11] 4,292,456

[45] Sep. 29, 1981

[54] OXYDEHYDROGENATION PROCESS FOR PREPARING INDENES

[75] Inventor: Oliver A. Kiikka, Willoughby, Ohio

[73] Assignee: The Standard Oil Co., Cleveland, Ohio

[21] Appl. No.: 108,259

[22] Filed: Dec. 28, 1979

[51] Int. Cl.$^3$ ............................................. C07C 5/32
[52] U.S. Cl. ................................. 585/431; 585/400; 585/410; 585/430; 585/433; 585/443; 585/444
[58] Field of Search ................ 585/27, 319, 320, 361, 585/400, 410, 415, 422, 430, 431, 433, 443, 444

[56] References Cited

U.S. PATENT DOCUMENTS

| | | | |
|---|---|---|---|
| 2,519,577 | 8/1950 | Ipstieff | 585/410 |
| 2,763,701 | 9/1956 | Hoffmann et al. | 585/400 |
| 2,984,692 | 5/1961 | Lederle | 585/400 |
| 3,183,249 | 5/1965 | Weise | 585/360 |
| 3,502,736 | 3/1970 | Sato et al. | 585/443 |
| 3,728,406 | 4/1973 | Vrinssen et al. | 585/360 |
| 3,853,291 | 12/1974 | Feins | 208/216 PP |
| 3,887,631 | 6/1975 | Yaffe | 585/445 |
| 3,925,498 | 12/1975 | Stadig | 585/625 |
| 3,933,932 | 1/1976 | Vrieland et al. | 585/444 |
| 4,143,082 | 3/1979 | Bartek et al. | 585/437 |

OTHER PUBLICATIONS

Chem. Abs. 55, 16506b.
Chem. Abs. 74, 76220.
Chem. Abs. 75, 63494.

*Primary Examiner*—Curtis R. Davis
*Attorney, Agent, or Firm*—John E. Miller, Jr.; Herbert D. Knudsen; Larry W. Evans

[57] ABSTRACT

An oxydehydrogenation process for producing indene and substituted indenes from indene precursors more saturated than indene is described and comprises contacting said precursor with oxygen and a catalyst comprising cobalt oxide and molybdenum oxide at an elevated temperature above about 300° C. Preferably the reaction is conducted at a temperature of about 500°–650° C. for a period of from 0.1 to about 30 seconds.

11 Claims, No Drawings

OXYDEHYDROGENATION PROCESS FOR PREPARING INDENES

BACKGROUND OF THE INVENTION

This invention relates to an improved oxydehydrogenation process for producing indene and substituted indenes, and more particularly, to an oxydehydrogenation process utilizing a composite catalyst comprising cobalt oxide and molybdenum oxide.

Indene is present in low concentrations (e.g. 12–16%) in ethylene or gas oil cracking coproducts, but is has been difficult to recover the indene in satisfactory yields and purity from these low concentration sources. Indene is a desirable raw material for preparing superior heat-resistant polymers.

The invention of this application is directed particularly to the preparation of indene and substituted indene from tetrahydroindene and substituted tetrahydroindene. Tetrahydroindene along with other products are formed in Diels-Alder reactions of butadiene with cyclopentadiene or its dimer, dicyclopentadiene. Substituted tetrahydroindenes are obtained when a substituted butadiene is used in the reaction. A considerable amount of research has been conducted and ublished on this reaction, and various suggestions have been made for optimizing the production of the various coproducts such as vinyl cyclohexene and vinyl norbornene.

The dehydrogenation of indene precursers such as tetrahydroindene into indene has been described in the art and generally is conducted in the presence of dehydrogenation promoting catalysts. In U.S. Pat. No. 4,143,082, the dehydrogenation of indene precursers into indene is accomplished by contacting the indene precurser in the presence of an oxygen donor with a phosphate catalyst at elevated temperature. These catalysts, described more fully in the patent, are salts of one of the phosphoric acids. Other types of dehydrogenation catalyst have been described in the literature, and such compounds include the metal oxides, metal salts such as the halides, phosphates, sulfates, molybdates, tungstates, etc. Generally, these catalysts are characterized as compounds containing a metal having a polyoxidation state, that is, a metal having at least two oxidation states in addition to the zero state. Examples of useful polyoxidation state metals include Ti, V, Cr, Mn, Co, Ni, Cu, Nb, Mo, Ru, etc.

In addition to the use of polyoxidative state metals, oxidation catalysts also may be combined with one or more monooxidation state metals which act as promoters, initiators, stabilizers and the like. The single oxidation state metal or metal compounds include the alkali metals, and polyvalent metals such as magnesium, aluminum, calcium, scandium, zinc, etc. The use of cobalt and molybdenum oxides promoted with potassium oxide in dehydrogenating indane to indene is reported in Czech Pat. No. 135,251. The catalyst bed contained 3% CoO, 10% $MoO_3$ and 0.3% $K_2O$. A review of the various catalysts useful in oxidative dehydrogenation of organic compounds is found in U.S. Pat. No. 3,925,498. U.S. Pat. No. 3,887,631 describes the oxidative dehydrogenation of hydrocarbons such as butene and ethylhexane by use of a catalyst consisting essentially of the oxides of molybdenum, cobalt and boron.

SUMMARY OF THE INVENTION

It now has been found that the highly desirable conversion of indene precursors more saturated than indene, particularly tetrahydroindene and substituted tetrahydroindene to indene and indene derivatives can be accomplished at desirable selectivity and yield by a method which comprises contacting said indene precursor with oxygen and a composite catalyst comprising cobalt oxide and molybdenum oxide at an elevated temperature. Generally, the reactants will be contacted with the catalyst at temperatures of from about 300°–650° C. for a period of from about 0.1 to 30 seconds, preferably from about 0.1 to 10 seconds.

DESCRIPTION OF THE PREFERRED EMBODIMENTS

In accordance with the present invention, indene and substituted indenes are produced from indene precursors more saturated than indene, e.g., tetrahydroindene and substituted tetrahydroindenes by oxydehydrogenation utilizing oxygen and a composite catalyst which comprises cobalt oxide and molybdenum oxide.

The indene precursors may be any compound more saturated than indene which can be oxydehydrogenated to indene or a substituted indene. The precursors may be alkyl or alkenyl enzenes such as n-propyl benzene or cumene, or substituted or unsubstituted bicyclic indene precursors more saturated than indene. The substituted bicyclic compounds can contain one or more alkyl or alkenyl groups having from one to four carbon atoms or can contain phenyl groups attached to one or both rings of the bicyclic compound. The substituted indenes obtained from these precursors normally have the corresponding alkyl, alkenyl or phenyl groups attached although there may be fewer groups or fewer carbon atoms in the groups.

Examples of bicyclic precursors which may be oxydehydrogenated in accordance with the invention include indane, alkyl (especially methyl) indanes in which the alkyl groups have from 1 to 4 carbon atoms, tetrahydroindene (especially the bicyclo(4.3.0)nona-3,7-diene isomer), alkyl tetrahydroindenes in which the alkyl groups have from 1 to4 carbon atoms, hexahydroindene, hexahydroindane and vinyl norbornene (5-vinyl bicyclo(2.2.1)-2-heptene).

In carrying out the process of the invention, the precursor such as tetrahydroindene or substituted tetrahydroindene is contacted with oxygen and a composite catalyst which comprises cobalt oxide and molybdenum oxide at an elevated temperature for a period of from about 0.1 to 30 seconds. The useful cobalt-molybdenum catalysts are commercially available from a variety of sources including the Nalco Chemical Company, Houston, Texas, and American Cyanamid Company, Bound Brook, New Jersey. These catalysts generally are contained on a support material such as carbon or alumina. U.S. Pat. No. 3,853,791 describes a variety of methods for preparing cobalt-molybdenum oxide catalysts on an alumina support.

The catalysts which are useful in the present invention generally contain from about 1–8% cobalt and from about 8–20% of molybdenum, the percentages being by weight based on the weight of the composite and expressed as the metal oxides. The term alumina support as used in the art and in this application describes substantially pure alumina or alumina containing minor amounts, for example up to about ten weight percent, of known stabilizers such as silica. The chemical analysis of a typical commercially available cobalt-molybdenum catalyst (Nalco Sphericat 477) is as follows: $MoO_3$, 12.5%; CoO, 3.5%; $Na_2O$, 0.08%; Fe, 0.03%; $SiO_2$, 1.5%; and $Al_2O_3$, balance.

The precursors are contacted in the vapor state with the oxygen and the catalyst at an elevated temperature generally from about 300° to about 650° C. and preferably from about 500° to about 650° C. The contact time can range from about 0.1 to about 30 seconds although shorter contact periods of from about 0.1 to 10 seconds are preferred. If the contact time is too long, back hydrogenation of the indene to tetrahydro and hexahydroindene is possible.

In one preferred embodiment, oxydehydrogenation of tetrahydroindene is conducted over a potassium oxide promoted cobalt-molybdenum catalyst and steam at 0.9 lb/lb tetrahydroindene. The conversion of tetrahydroindene is 96.5% at a temperature of 515° C. and about one second contact time. The indene/indane ratio under these conditions is 6.55.

Although the cobalt-molybdenum catalysts described above are useful in the oxydehydrogenation reactions of the invention, it has been found that improved results are obtained when the promoters for the catalysts are included. It appears that the presence of the promoter reduces the extent of catalyst fouling caused at least in part by the formation of carbon deposits on the catalyst during the dehydrogenation reaction.

Alkaline metal compounds can be included with the catalyst in limited quantities as a promoter for the catalytic reaction. Examples of particularly useful promoters include potassium oxide, cesium oxide and rubidium oxide. Although the optimum type and quantity of promoter may vary depending upon the reaction conditions and the reactants, the use of potassium oxide in quantities of up to 2% or more generally is preferred.

The size of the catalyst particles is not critical and can vary between wide limits. For example, the catalyst particle size may be extremely small (e.g., microspheroidal) so that the catalyst can be employed in a fluid-bed reactor or the catalyst can be significantly larger in particle size so that the catalyst can be employed in a fixed-bed reactor.

As an oxygen donor, elemental oxygen, $O_2$ generally is employed. In particular, air is normally employed as a feed since it is the cheapest and the most convenient oxygen donor or source. Other compounds which will serve as oxygen donors and dehydrogenation reactions can be employed such as, for example, $SO_2$, COS and HOCl.

The amount of oxygen fed to the reaction vessels should be at least the stoichiometric amount necessary to react with all of the hydrogen to be withdrawn from the indene precursor feed. Of course, less than stoichiometric amounts can be fed to the reactor, but this can decrease the efficiency of the process. Preferably, the amount of oxygen donor fed to the reaction vessel is at least twice, preferably two to five times, the stoichiometric amount necessary to react all of the hydrogen withdrawn from the indene precursor.

In addition to the foregoing components, a gaseous promoter known to increase oxidation rates also can e fed to the reaction vessel for improving the efficiency of the dehydrogenation reaction. For example, certain compounds such as halides (gaseous HCl, HBr, $Cl_2$, $Br_2$ and alkyl halides containing one to five carbon atoms) promote various types of dehydrogenation reactions. In accordance with the present invention, the gaseous promoters are fed to the reaction vessel generally along with the oxygen donor for increasing the efficiency of the dehydrogenation reaction. When a gaseous promoter is employed, it is preferable that the amount be less than 10%.

The materials fed to the reaction vessels also can contain a gaseous diluent. Any gas inert to the reaction and catalyst can be employed as the diluent. Preferred diluents are $N_2$, $CO_2$, $H_2O$, combustion gases and light hydrocarbon gases (for example, methane). When the oxygen donor is $O_2$, the amount of inert diluent should be from 0 to 20 times the amount of $O_2$ fed to the reaction vessel. When other oxygen donors are employed, a stoichiometrically corresponding amount of inert diluent can be employed. The dehydrogenation reactions can be carried out either in fixed-bed or fluid-bed reactors. In fixed-bed reactors, the liquid hourly space velocity of the feed is from 0.01 to 10 and preferably from 0.05 to 1 hour$^{-1}$. The contact time generally is from about 0.1 to 30 seconds and preferably from 0.1 to 10 seconds. The reaction pressure is normally maintained at approximately atmospheric pressure, although lower or higher pressures can be employed if desired.

The efficacy of the method of the invention for producing indene and substituted indenes from indene precursors is illustrated in the following examples which are conducted in a 20 cc. fixed bed reactor. The general procedure is as follows. Nitrogen is bubbled through a saturator containing the indene precursor and water. This mixed feed, along with combustion air, enters the reactor. Both nitrogen and air are fed through calibrated rotameters. The rates, including product of gas, are measured by timing bubble travel in a 50 cc. burette. The feed rate is determined by weighing the saturator before and after a series of runs knowing the on-stream time. The residual feed is split into a hydrocarbon-water fraction to determine the actual amounts of each feed.

The reactor effluent is collected in two knock-out flasks connected in series and mounted in an ice bath. The second flask contains distilled water. Most of the liquid product recovered generally is condensed in the first flask (90+%). This product is analyzed by gas chromatography and no solvents or dilution is used. The retention times are confirmed either by spiking the liquid product of running separately high purity knowns.

The catalyst used in the following examples 1–5 is Nalcomo 477, an extruded cobalt molybdenum catalyst available from Nalco Chemical Company analyzing, on a dry basis, 12.5% $MoO_3$, 3.5% CoO, 0.08% $Na_2O$, 0.03% Fe, 1.5% $SiO_2$ and the balance $Al_2O_3$. The catalyst is used as received and does produce indene over a temperature range of from about 350° to about 460° C. although the best indene to indane ratio obtained is about 2.0.

Example 6 which is summarized in the following table utilizes Sphericat 477 promoted with 1% potassium oxide. This catalyst has the identical analysis as the Nalcomo 477 but is spherical in shape. As can be seen from the results in the table, the use of the potassium oxide promoted catalyst at the higher temperature of about 515° C. results in a higher conversion and indene/indane ratio than is obtained with unpromoted catalyst at lower temperatures. The results which are exhibited by the examples 1–6 demonstrate the observed phenomenon that as the temperature of the oxydehydration reaction is raised, increasing amounts of indene are formed and the indene to indane ratio increases significantly. It is expected, therefore, that at higher temperatures such as 550°-650° C., the yield of indene and indene to indane ratio will be even further increased.

The results summarized in the following table with respect to examples 7 and 8 demonstrate that indene can be prepared by the oxydehydrogenation (more specifically, oxydehydrocyclization) of n-propylbenzene and cumene respectively.

When the above-described dehydrogenation reactions of tetrahydroindene are conducted in the absence of added oxygen, the conversion of tetrahydroindene remains high, but the amount of indene in the product mixture generally is less at a given reaction temperature.

| Example | Feed | Catalyst | Temp °C. | THI/H$_2$O/Air/N$_2$ | Conversion (%) | Indene (%) | Indane (%) | Indene/Indane | Indene Selectivity % |
|---|---|---|---|---|---|---|---|---|---|
| 1 | THI | Nalcomo 477 | 460° | 1/4.8/18.7/16.5 | 92.3 | 54.5 | 28.6 | 1.9 | 62.6 |
| 2 | THI | Nalcomo 477 | 350 | 1/6.0/10.9/17.4 | 91.7 | 41.6 | 45.28 | 0.92 | 48.0 |
| 3 | THI | Nalcomo 477 | 405 | 1/6.0/10.9/17.4 | 46.8 | 26.0 | 20.34 | 1.3 | 58.7 |
| 4 | THI | Nalcomo 477 | 350 | 1/5.1/17.0/17.0 | 60.8 | 32.09 | 28.60 | 1.12 | 55.9 |
| 5 | THI | Nalcomo 477 | 405 | 1/5.1/17.0/17.0 | 37.7 | 24.72 | 12.29 | 2.01 | 69.3 |
| 6 | THI | Sphericat 477[1] | 515 | 1/4.2/5.9/15.5 | 96.5 | 75.36 | 11.52 | 6.55 | 82.9 |
| 7 | n-PB[4] | Sphericat 477[1] | 515 | 1/11.6/5.2/28.0 | 73.7 | 34.9 | 15.69 | 2.22 | 48.4[2] |
| 8 | cumene | Sphericat 477[1] | 515 | 1/7.1/4.5/18.9 | 73.4 | 8.78 | 4.05 | 2.16 | 18.4[3] |

[1]Regenerated and promoted with 1% K$_2$O
[2]Product also contained 25.6% unreacted n-propyl benzene and 6% allyl benzene
[3]Product also contained 25.25% unreacted cumene, 50.45% alpha-methylstyrene and 2.33% ethyl benzene
[4]n-propyl benzene

I claim:

1. An oxydehydrogenation process for producing unsubstituted or substituted indenes from at least one unsubstituted or substituted indene precursor more saturated than indene which comprises contacting said indene precursor and an oxygen donor with a catalyst comprising cobalt oxide and molybdenum oxide at a temperature above about 300° C.

2. The process of claim 1 wherein the indene precursor is hexahydroindene, tetrahydroindene, substituted tetrahydroindenes containing up to 4 carbon atoms in the substituent, n-propyl benzene or cumene.

3. The method of claim 1 wherein the temperature is between about 500°-650° C. and the contact time is from 0.1 to 30 seconds.

4. The process of claim 1 wherein the catalyst is promoted with an alkali or alkaline earth metal oxide.

5. The process of claim 1 wherein the catalyst comprises from about 8 to 20% molybdenum oxide and from about 1 to about 8% of cobalt oxide on a support.

6. The process of claim 4 wherein the promoter is potassium oxide, cesium oxide or rubidium oxide.

7. The process of claim 1 wherein the oxygen donor is air.

8. The process of claim 1 wherein the catalyst comprises from about 8 to 20% of molybdenum oxide, from 1 to 8% of cobalt oxide and from about 1 to 2% of silica on an aluminum support.

9. The process of claim 1 wherein the temperature is from about 500°-650° C. and the contact with the catalyst is for a period of about 0.1 to 10 seconds.

10. An oxydehydrogenation process for preparing indene which comprises contacting tetrahydroindene with oxygen and a catalyst comprising from about 1 to 8% of cobalt oxide, 8 to 20% of molybdenum oxide and 1 to 2% of silica on an alumina support at a temperature of from about 500°-650° C. for a period of about 0.1 to 10 seconds.

11. The process of claim 10 wherein the oxydehydrogenation is promoted with potassium, cesium or rubidium oxide.

* * * * *